(12) United States Patent
Vrabec et al.

(10) Patent No.: US 11,819,687 B2
(45) Date of Patent: Nov. 21, 2023

(54) PARTIAL NERVE CONDUCTION BLOCK USING A SEPARATED INTERFACE NERVE ELECTRODE (SINE)

(71) Applicant: Case Western Reserve University, Cleveland, OH (US)

(72) Inventors: Tina L. Vrabec, Cleveland, OH (US);
Kevin L. Kilgore, Cleveland, OH (US);
Niloy Bhadra, Cleveland, OH (US);
Laura Shaw, Cleveland, OH (US);
David Roberts, Cleveland, OH (US);
Narendra Bhadra, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 251 days.

(21) Appl. No.: 16/615,210

(22) PCT Filed: May 24, 2018

(86) PCT No.: PCT/US2018/034383
§ 371 (c)(1),
(2) Date: Nov. 20, 2019

(87) PCT Pub. No.: WO2018/218018
PCT Pub. Date: Nov. 29, 2018

(65) Prior Publication Data
US 2020/0155832 A1      May 21, 2020

Related U.S. Application Data

(60) Provisional application No. 62/611,041, filed on Dec. 28, 2017, provisional application No. 62/510,465, filed on May 24, 2017.

(51) Int. Cl.
*A61N 1/05* (2006.01)
*A61N 1/20* (2006.01)
*A61N 1/36* (2006.01)

(52) U.S. Cl.
CPC ............. *A61N 1/0551* (2013.01); *A61N 1/20* (2013.01); *A61N 1/36067* (2013.01); *A61N 1/36103* (2013.01)

(58) Field of Classification Search
CPC .... A61N 1/0551; A61N 1/20; A61N 1/36067; A61N 1/36103; A61N 1/306; A61N 1/0436
See application file for complete search history.

(56) References Cited

U.S. PATENT DOCUMENTS

| | | | |
|---|---|---|---|
| 9,008,800 B2* | 4/2015 | Ackermann, Jr. ... | A61N 1/0551 607/118 |
| 2014/0324129 A1 | 10/2014 | Franke et al. | |
| 2016/0101286 A1 | 4/2016 | Bhadra et al. | |

FOREIGN PATENT DOCUMENTS

WO     2009058258 A1     5/2009

OTHER PUBLICATIONS

Rizzo, M. A., et al. "Prevalence and treatment of spasticity reported by multiple sclerosis patients." Multiple Sclerosis Journal 10.5 (2004): 589-595.

(Continued)

*Primary Examiner* — Mark W. Bockelman
(74) *Attorney, Agent, or Firm* — TAROLLI, SUNDHEIM, COVELL & TUMMINO, LLP

(57) ABSTRACT

Systems and methods that deliver a continuous partial nerve conduction block are described. A waveform generator can configure one or more direct current (DC) waveforms to provide a continuous partial nerve conduction block. One or more electrodes can deliver the one or more DC waveforms to provide the partial block to the neural structure. Feedback can be provided to the waveform generator related to the partial block. The feedback includes monitoring a property associated with the partial block and altering a parameter (Continued)

associated with the one or more direct current waveforms in response to the property associated with the partial block.

14 Claims, 12 Drawing Sheets

(56) References Cited

OTHER PUBLICATIONS

Amatya, Bhasker, et al. "Non pharmacological interventions for spasticity in multiple sclerosis." Cochrane database of systematic reviews 2 (2013).

Lundstrom, Erik, et al. "Four-fold increase in direct costs of stroke survivors with spasticity compared with stroke survivors without spasticity: the first year after the event." Stroke 41.2 (2010): 319-324.

Naples, Gregory G., et al. "A spiral nerve cuff electrode for peripheral nerve stimulation." IEEE transactions on biomedical engineering 35.11 (1988): 905-916.

Baron, Ralf. "Neuropathic pain: a clinical perspective." Sensory Nerves. Springer, Berlin, Heidelberg, 2009. 3-30.

Tiede, Jeffrey, et al. "Novel spinal cord stimulation parameters in patients with predominant back pain." Neuromodulation: Technology at the Neural Interface 16.4 (2013): 370-375.

Franke, M., N. Bhadra, and K. J. Gustafson. "Chronic bladder voiding after SCI using electric HFAC pudendal nerve block." Neural Interfaces Conference. 2012.

Stokvis, Annemieke, J. Henk Coert, and Johan W. van Neck. "Insufficient pain relief after surgical neuroma treatment: prognostic factors and central sensitisation." Journal of plastic, reconstructive & aesthetic surgery 63.9 (2010): 1538-1543.

Koch, Horst, et al. "Treatment of painful neuroma by resection and nerve stump transplantation into a vein." Annals of plastic surgery 51.1 (2003): 45-50.

Dormandy, John, Ludger Heeck, and Stella Vig. "Major amputations: clinical patterns and predictors." Seminars in vascular surgery. vol. 12. No. 2. 1999.

Franke, M., et al. "Chronic bladder control post SCI via electric KHFAC pudendal nerve block." IEEE EMBS Conference Neural Engineering. 2013.

Lin, Yin-Tsong, et al. "Dual-channel neuromodulation of pudendal nerve with closed-loop control strategy to improve bladder functions." J Med Biol Eng 34.34 (2014): 82-9.

Ackermann Jr, D. Michael, et al. "Separated interface nerve electrode prevents direct current induced nerve damage." Journal of neuroscience methods 201.1 (2011): 173-176.

Written Opinion of International Search Report for Corresponding International Application No. PCT/US2018/034383, pp. 1-3.

\* cited by examiner

PARTIAL NERVE CONDUCTION BLOCK USING A SEPARATED INTERFACE NERVE ELECTRODE (SINE)

RELATED APPLICATION

This application claims priority to U.S. Provisional Application Ser. No. 62/510,465, filed May 24, 2017, entitled "PARTIAL POLARIZING NERVE BLOCK: CHALLENGES AND OPPORTUNITIES", and to U.S. Provisional Application Ser. No. 62/611,041, filed Dec. 28, 2017, entitled "PARTIAL BLOCK USING THE SEPARATED INTERFACE NERVE ELECTRODE (SINE)". The entireties of these applications are hereby incorporated by reference for all purposes.

GOVERNMENT SUPPORT

This invention was made with government support under R01-NS-089530 awarded by the National Institutes of Health, National Institute of Neurological Disorders and Stroke. The government may have certain rights in the invention.

TECHNICAL FIELD

The present disclosure relates generally to partial nerve conduction block and, more specifically, to systems and methods that deliver a continuous partial nerve conduction block for an extended period of time.

BACKGROUND

Many neurological disorders are characterized by unwanted neurological activity, which includes pathological effects on end organs. For example, such pathological effects can include autonomic disorders, spasticity, and chronic pain. Pharmacological methods have long been the standard for treating such pathological effects. However, such pharmacological methods have several drawbacks, including the presence side effects and interactions with other medications that limit the patients that can be treated; the inability to modulate the dosage in real time; and the like.

An alternative to the pharmacological methods is electrical nerve block, which has the capacity to provide immediate block, immediate reworkability, and real time modulation. These features allow electrical nerve block to provide personalized medicine to the patient. The application of an electrical field to a nerve has been shown to produce an electrical block of action potential conduction (or "nerve conduction block"). The mechanism for this nerve conduction block can be either depolarization or hyperpolarization depending on which ion channels are effected by the electric field. Kilohertz frequency alternating current (KHFAC) produces a steady state depolarization while direct current (DC) can be used to generate either a depolarization or hyperpolarization depending on the polarity of the signal. A drawback of KHFAC drawback is that the application of KHFAC is preceded by a burst of spurious activity. Direct current (DC) has been shown to provide nerve conduction block without spurious activity as long as a ramp is used to bring the DC to the block threshold. Therefore, DC is generally the preferred way to deliver the nerve conduction block.

The effectiveness of the nerve conduction block depends on the magnitude of the electrical field that is applied to the nerve. The lowest electrical field that results in a functional block of the nerve is referred to as the "block threshold". Depending on the application, a functional block is achieved by targeting different nerve fibers for each application. Due to their size, motor fibers are blocked with lower block thresholds than smaller fibers, such as pain fibers or autonomic fibers. Although complete nerve conduction block is achieved at the block threshold, there are applications that would be well suited to the use of a partial nerve conduction block. An example of an application that would be well suited to the use of partial nerve conduction block is a solution that can minimize spasticity while maintaining muscle tone allowing for previously unattainable functional improvements. However, with application of DC, continuous partial nerve conduction block cannot be achieved.

SUMMARY

The present disclosure relates generally to partial nerve conduction block and, more specifically, to systems and methods that deliver a continuous partial nerve conduction block for an extended period of time.

In an aspect, the present disclosure can include a system that can deliver a continuous partial nerve conduction block. The system includes a waveform generator to generate one or more direct current (DC) waveforms configured to provide a partial block to a neural structure. One or more electrodes to deliver the one or more direct current waveforms to provide the partial block to the neural structure. A feedback device to provide feedback to the waveform generator related to the partial block. The feedback is based on a monitored property associated with the partial block and an altered parameter associated with the one or more direct current waveforms in response to the property associated with the partial block.

In a further aspect, the present disclosure can include a method delivering a continuous partial nerve conduction block. A waveform generator can configure one or more DC waveforms to provide a partial block to a neural structure. The one or more DC waveforms can be delivered through one or more electrodes to provide the partial block to the neural structure. Feedback can be provided to the waveform generator related to the block. The providing of the feedback can include monitoring a property associated with the partial block; and altering a parameter associated with the one or more direct current waveforms in response to the property associated with the partial block.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
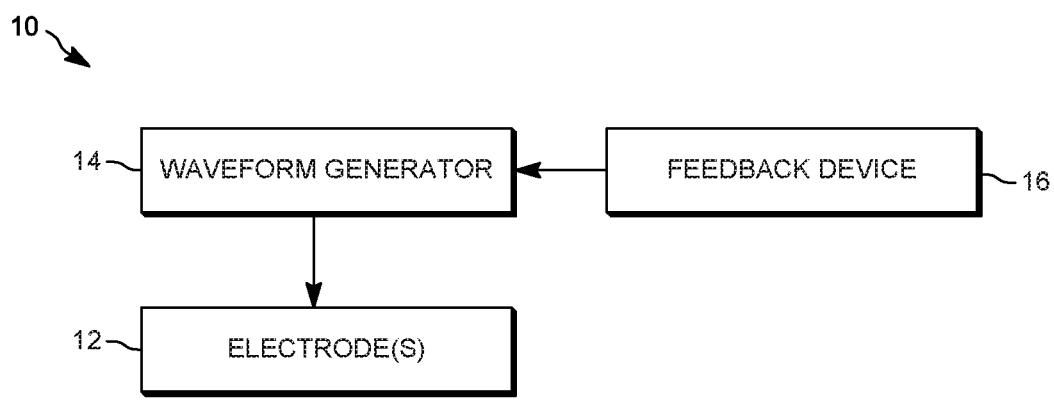
FIG. 1 is a diagram showing a system that delivers a continuous partial nerve conduction block for an extended period of time in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "nerve conduction block" can refer to the attenuation of conduction in at least one nerve fiber due to a change in the electric field caused by application of an electrical signal to the nerve. In some instances, the nerve conduction block can provide a "complete" attenuation of conduction in all nerve fibers in the nerve. However, in other instances, the nerve conduction block can provide a "partial" attenuation of conduction in a portion of the nerve fibers in the nerve.

As used herein, the term "electrode" refers to a conductor through which electricity enters or leaves an object, substance, or region.

As used herein, the term "separated interface nerve electrode (SINE)" can refer to an electrode design in which an electrode is separated from a nerve interface by a column of electrolyte. The SINE uses ionic coupling, which separates the electron flow and the ionic flow. Because the reactants of the electrochemical reaction are separated from the nerve interface, the damaging electrochemical reaction products are separated from the nerve interface. Accordingly, the SINE provides a less harmful way to deliver direct current (DC) to tissue to perform nerve conduction block.

As used herein, the term "nerve cuff" refers to an electrode design in which two or more contacts are included in a housing that surrounds the nerve. One example of a nerve cuff is a carbon ink cuff electrode (which can include platinum foil contacts coated with carbon ink to increase charge capacity).

As used herein, the term "electrical signal" can refer to a function that conveys information about the behavior or attributes of an electric phenomenon, such as electric current, that varies with time and/or space. For example, the electrical signal can be an alternating current (e.g., kilohertz frequency alternating current) signal and/or a direct current signal.

As used herein, the terms "direct current" or "DC" can refer to a unidirectional flow of electric charge. In some instances, the DC can have a plateau of a cathodic polarity or an anodic polarity. The DC can further be represented as a waveform that includes a ramp from a zero position to the plateau. In some instances, the waveform can also include a ramp down from the plateau position to the zero position. In still other instances, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, the term "direct current block" or "DC block" can refer to the application of a direct current pulse with a polarity configured depolarization or hyperpolarization to cause change in the electric field sufficient to alter conduction in the nerve.

As used herein, the terms "alter" or "altering", when used with reference to nerve conduction, can refer to affecting or changing a manner in which action potentials are conducted in a nerve. In some instances, nerve conduction can be altered by extinguishing an action potential at some point as it travels along the nerve (also referred to as "blocking" nerve conduction). In other instances, nerve conduction can be altered by increasing the activation threshold of a nerve and/or decreasing the conduction velocity of a nerve (also referred to as "attenuating" nerve conduction).

As used herein, the term "neural structure" can refer to tissue related to the central nervous system, peripheral nervous system, autonomic nervous system, and enteric nervous system. The term neural structure, in some instances, can include one or more nerves and/or neural fibers.

As used herein, the term "nerve" can refer to one or more fibers that employ electrical and chemical signals to transmit information. A nerve can refer to either a component of the central nervous system or the peripheral nervous system. For example, in the peripheral nervous system a nerve can transmit motor, sensory, autonomic, and/or enteric information from one body part to another As used herein, the term "fiber" can refer to an axon of a neuron.

As used herein, the term "neurological disorder" can refer to a condition or disease characterized at least in part by abnormal conduction in one or more nerves. The neurological disorder can be in the motor system, the sensory system, and/or the autonomic system.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. Overview

Although complete nerve conduction block can easily be achieved, some applications benefit from only partial nerve conduction block. Accordingly, the present disclosure relates generally to partial nerve conduction block. Direct current (DC) waveforms are generally the preferred electrical waveform to provide nerve conduction block because DC waveforms can be configured to eliminate an onset response, and the partial nerve conduction block can be established when the electric field produced is less than a block threshold. However, DC waveforms have drawbacks in terms of generating harmful reaction products. These reaction products can be eliminated using different delivery schemes, including changing the waveform to a charge balance polarizing current (CBPC) waveform or using a different electrode like a separated interface nerve electrode (SINE), which has the ability to provide polarizing current nerve conduction block while separating any potentially damaging reactants from the nerve. While both the CBPC waveform when applied using multiple contacts in a carousel fashion and the SINE can provide a continuous full nerve conduction block, both the CBPC waveform and the SINE are generally unable to provide a continuous partial nerve conduction block.

The present disclosure relates, more specifically, to systems and methods that deliver a continuous partial nerve conduction block for an extended period of time. With CBPC, modulation of the DC waveform delivered by each contact of the multiple contacts can lead to a continuous partial nerve conduction block. Similarly, with SINE, the current level of the DC waveform can be changed based on a physiological output (e.g., force due to the block). Accordingly, both the CBPC and SINE can be modulated to achieve the continuous partial nerve conduction block.

III. Systems

One aspect of the present disclosure can include a system 10 (FIG. 1) that can deliver a continuous partial nerve conduction block for an extended period of time. Traditionally, it has been difficult to maintain a stable partial block at a given level for an extended period of time. The system 10 enables the stable partial block to be maintained for an extended period of time using control techniques.

The partial nerve conduction block can be accomplished by delivering one or more direct current (DC) waveforms through one or more electrodes 12 to a nerve. For example, the DC waveforms can include a constant level direct current waveform, a varying level direct current waveform, a direct current waveform followed by a recharge phase, or a direct current waveform in combination with a high frequency signal. The recharge phase can be any shape as long as it is charge balance—like a square, a rectangle, a trapezoid, etc. The partial nerve conduction block can alter conduction in less than all of the fibers in the neural structure.

In one example, the neural structure can be a peripheral nerve (e.g., motor, sensory, and/or autonomic/enteric) or a nerve or nervous tissue comprising the central nervous system (e.g., brain and/or spinal cord). The DC nerve conduction block can be used to treat various neurological disorders including, but not limited to, chronic neuropathic pain or muscle spasticity. The DC nerve conduction block can also be used to modulate or inhibit neural activity in the autonomic or enteric system. Additionally, the DC nerve conduction block can be used to manage regional applications, like chronic headache management or bladder control.

The system 10 can include a waveform generator 14, which is coupled to one or more electrodes 12 (including a source electrode and a return electrode), and a feedback device or mechanism 16. In some instances, the coupling of the waveform generator 14 to each of the one or more electrodes 12 and to the feedback device 16 can be via a wired connection (e.g., via a percutaneous wire or a subcutaneous wire). In other instances, the coupling of the waveform generator 14 to the one or more electrodes 12 and/or to the feedback device 16 can be via a wireless connection. In still other instances, the coupling of the waveform generator 14 to the one or more electrodes 12 and/or to the feedback device 16 can be via a connection that is both wired and wireless.

The waveform generator 14 can be configured or programmed to generate one or more DC waveforms that can provide a partial block to the target neural structure. Accordingly, the waveform generator 14 can be any device configured or programmed to generate the specified one or more DC waveforms for application to the target neural tissue to achieve an alternation in conduction thereof. One example of a waveform generator 14 is a battery-powered, portable generator (the waveform generator 14 positioned externally). Another example of a waveform generator 14 is an implantable generator (IPG) (at least a portion of the waveform generator 14 positioned subcutaneously). It will be appreciated that the waveform generator 14 can include additional components to selectively configure the current waveform, such as an amplitude modulator (not shown).

The waveform generator 14 can generate, configure, and deliver the one or more DC waveforms to the one or more electrodes 12 (e.g., source electrodes), which can provide the partial block to the neural structure. In some instances, the generated DC can have an anodic polarity or a cathodic polarity, and an amplitude sufficient to cause the partial nerve conduction block. As one example, the waveform generator 14 can be configured or programmed to generate one or more monophasic DC waveform. In other examples, the waveform generator 14 can be configured or programmed to generate one or more DC having a biphasic waveform, with one phase cathodic and one anodic. In this case, the altering DC can be delivered to the nerve in the first phase for a specific period of time, while a second phase having an opposite polarity can reduce or eliminate unwanted effects generated by the first phase. In some instances, a generated biphasic DC waveform can be a charge-balanced biphasic waveform that produces zero net charge. In other instances, a series of DC waveforms can be applied as a carousel, where each of a plurality of electrode contacts applies one of the series of DC waveforms.

Figure 2:
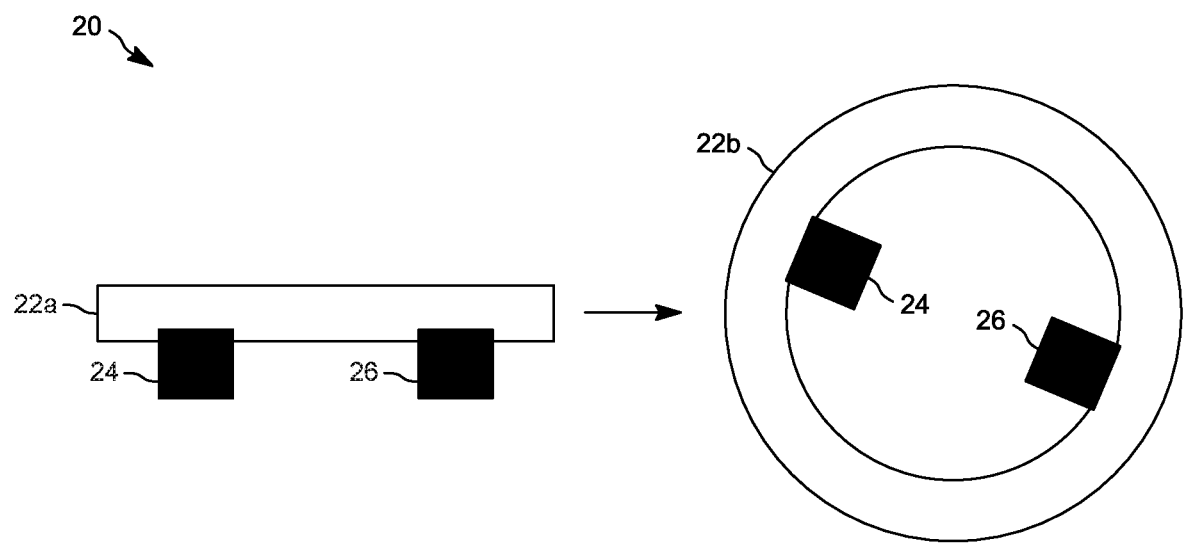
FIG. 2 is schematic diagram of a nerve cuff electrode with two electrode contacts that can be used by the system in FIG. 1.
Figure 3:
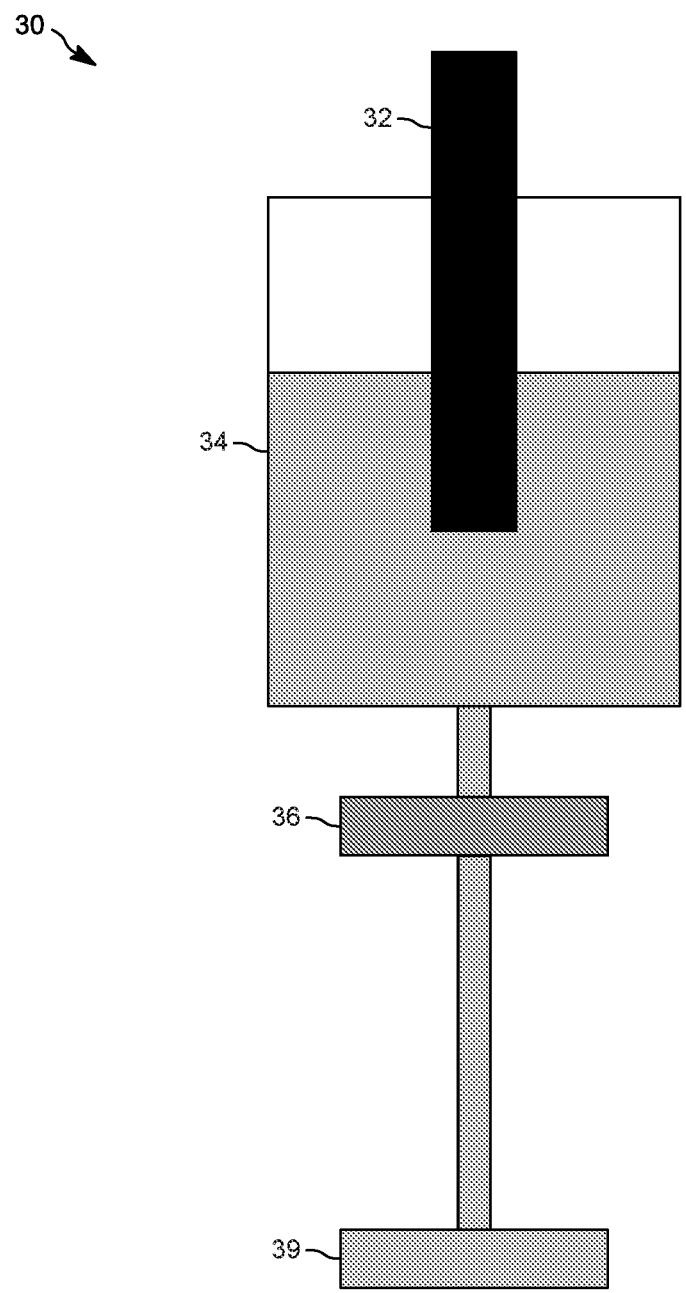
FIG. 3 is a schematic diagram of a separated interface nerve electrode (SINE) that can be used by the system in FIG. 1.

The one or more electrodes 12 can include one or more source electrodes and a return electrode. In some instances, the one or more source electrodes can be two or more contacts of a nerve cuff (shown in FIG. 2 for example, with the cuff shown open 22a and closed 22b with contacts 24, 26). The contacts can be platinum foil covered by carbon ink. For example, the two or more contacts of the nerve cuff can deliver a carousel of biphasic DC waveforms. The carousel may be more well suited for chronic application to nerves that are deeper in the body. In other instances, the one or more source electrodes can include a separated interface nerve electrode (SINE), which separates a metal electrode 32 from a neural interface 39 by an electrolyte 34 and a stopper 36 to confine any reaction products away from the nerve. For example, the SINE can be used to deliver monophasic pulses to the neural structure and may be more appropriate to short term acute applications, such as post-operative pain.

A feedback device 16 can provide feedback to the waveform generator 14 related to the partial block. Addition of the feedback device 16 to the system 10 enables the stable partial block to be maintained for an extended period of time. The feedback that the feedback device 16 receives can be based on a monitored property associated with the partial block and an altered parameter associated with the one or more DC waveforms in response to the property associated with the partial block. In other words, the property associated with the partial block can be monitored and the parameter associated with the one or more DC waveforms can be altered in response to the monitored property. For example, the monitored property can be a physiological output controlled by the neural structure produced in response to application the partial block, including (but not limited to) a force. The parameter associated with the one or more direct current waveforms can include a current level, a recharge level, or a spacing between pulses in the blocking phases, or the like associated with the one or more direct current waveforms.

The feedback device 16 can allow for automatic and/or manual control. As an example, the feedback device 16 can be a hardware controller that includes a non-transitory memory and a processor. In this example, the hardware controller can be a simple proportional controller or a sophisticated feedback controller that uses a model configured to estimate at least one dynamic system property. The dynamic system property can be of the neural structure, the one or more DC waveforms, and/or the one or more electrodes.

IV. Methods

Another aspect of the present disclosure can include a method 40 (FIG. 4) for delivering a continuous partial nerve conduction block for an extended period of time. The method 50 of FIG. 5 extends the method 40 and illustrates an example of how feedback is provided. The methods 40 and 50 can be executed using the system 10 shown in FIG. 1 and described above.

The methods 40 and 50 are illustrated as process flow diagrams with flowchart illustrations. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

Figure 4:
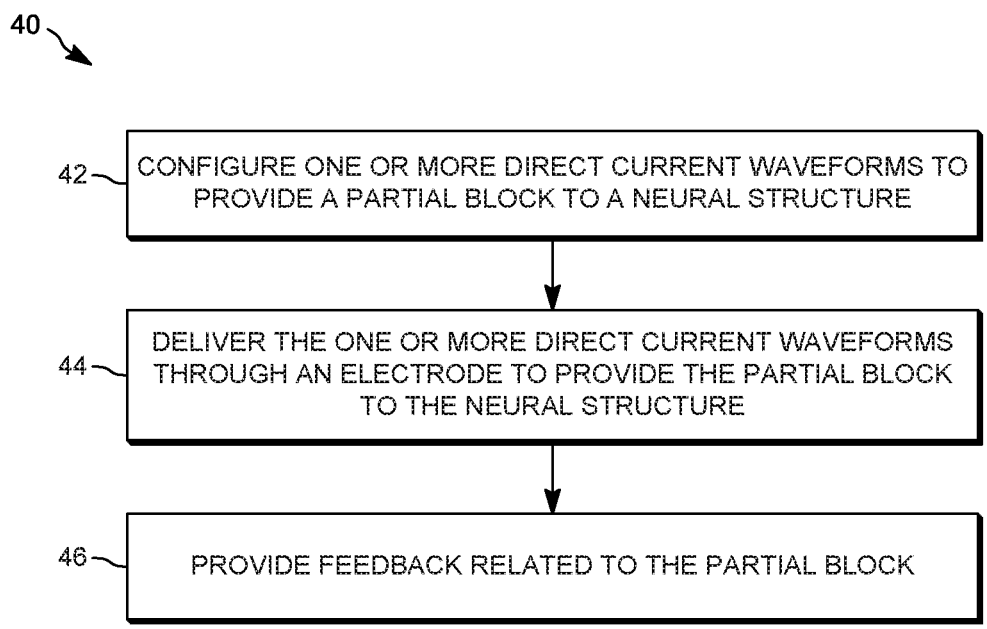
FIG. 4 is a process flow diagram illustrating a method for delivering a continuous partial nerve conduction block for an extended period of time according to another aspect of the present disclosure.

Referring now to FIG. 4, illustrated is a method 40 for delivering a continuous partial nerve conduction block for an extended period of time. At Step 42, one or more direct current (DC) waveforms can be configured (e.g., by waveform generator 14) to provide a partial block to a neural structure. In some examples, the neural structure can be a peripheral nerve or neural fibers (e.g., motor, sensory, enteric, and/or autonomic) or a nerve or nervous tissue comprising the central nervous system (e.g., brain and/or spinal cord). The waveform generator can generate and configure the DC to be applied to the neural structure. The DC can be configured for the specific applications, such as based on the block threshold of the target neural structure, so that the DC can have an amplitude sufficient to alter transmission of a portion of the action potentials in the target neural structure. For example, the DC can be anodic or cathodic and have an amplitude sufficient to generate an electric field that is able to alter transmission of action potentials in the target neural structure according to the partial block required. In some instances, the DC can be applied as a biphasic waveform, with the second phase operable to reverse the charge delivered by the first phase or as a carousel). In other instances, the DC can be applied as a monophasic waveform of a certain polarity.

At Step 44, the one or more DC waveforms can be delivered through one or more electrodes (e.g., electrode(s) 12) to provide the partial block to the neural structure. In some instances, the one or more electrodes can include a separated interface nerve electrode (SINE). A portion of the SINE contacting a metal electrode can be filed with high surface area carbon to create a slurry, which can increase the charge capacity of the SINE. For example, the SINE confines reaction products close to the electrode so monophasic DC waveforms can be delivered to the nerve. In other instances, the one or more electrodes can include at least two electrode contacts in a nerve cuff. The at least two electrode contacts can be coated with a carbon ink to increase the charge capacity of the electrode contacts. As an example, each of the contacts can receive a complimentary DC waveform with a variable blocking phase followed by a s recharge phase to balance the charge.

At Step 46, feedback can be provided (e.g., to the waveform generator 14) related to the partial block. The feedback can be provided by a feedback device 16. In some instances, the feedback device 16 can allow for manual control. In other instances, the feedback device 16 can be a controller device with a non-transitory memory and a processor that can provide autonomous, automatic control (without requiring use intervention). As an example, the controller device can be a simple proportional controller. As another example, the controller device can be a sophisticated feedback controller that uses a model to estimate at least one dynamic system property associated with the one or more electrodes, the one or more DC waveforms, the neural structure, or the like. The model can, for example, estimate the dynamic system property using three or more inflection points.

Figure 5:
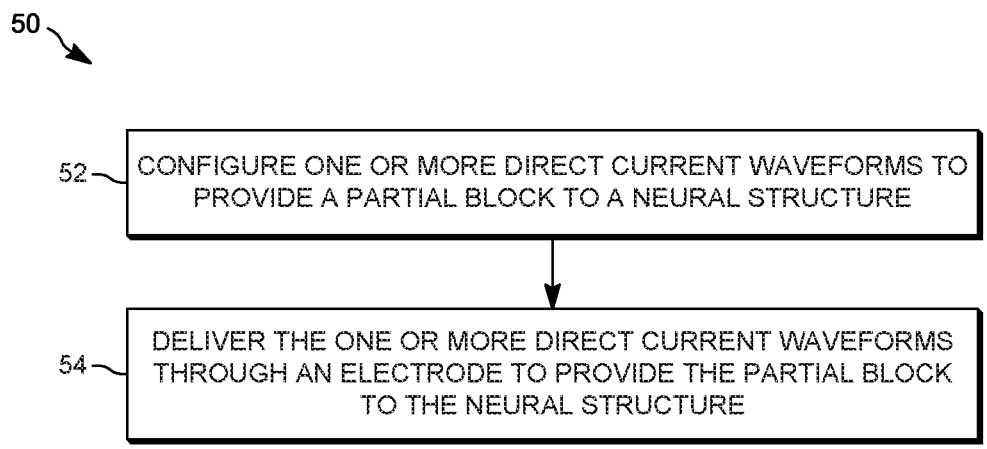
FIG. 5 is a process flow diagram illustrating a method for providing feedback according to the method of FIG. 4.

FIG. 5 gives an example 50 of the feedback that can be provided to the waveform generator. At 52, a property associated with the partial block can be monitored. The property associated with the partial block can be, for example, a physiological output controlled by the neural structure produced in response to application the waveform, which causes the partial block. For example, the physiological output can be a force generated by or associated with the neural structure. At 54, a parameter associated with the one or more DC waveforms can be altered in response to the property associated with the partial block. The altered parameter ensures that the physiological output remains constant. The parameter associated with the one or more DC waveforms can include a current level associated with the one or more DC waveforms, a recharge level associated with the one or more DC waveforms, or a spacing between pulses in the blocking phases associated with the one or more DC waveforms.

V. Experimental

A continuous partial nerve conduction block can be established using a carousel setup and/or a separated nerve interface electrode (SINE), as shown in the following experiments. It is important to note that the system dynamics of the application for which the partial block is applied have a significant impact on the ability to maintain a partial block. For example, the autonomic system generally has a slower response, which filters the effect of the block, while the motor system is much more responsive, so the control of the partial nerve block needs to be more complex to provide a consistent output.

The following experimental results are shown for the purpose of illustration only and are not intended to limit the scope of the appended claims.

Carousel Setup

Charge balance polarizing current (CBPC) nerve block can provide block without spurious activity, but when used with a single contact electrode can only provide a 10% duty cycle of block to non-block. When multiple contacts are used, however, continuous block can be achieved. A well-controlled partial block is possible during the plateau phase of the CBPC block. Modulation of each contact of a multiple contact solution should be able to produce a continuous partial block.

Figure 6:
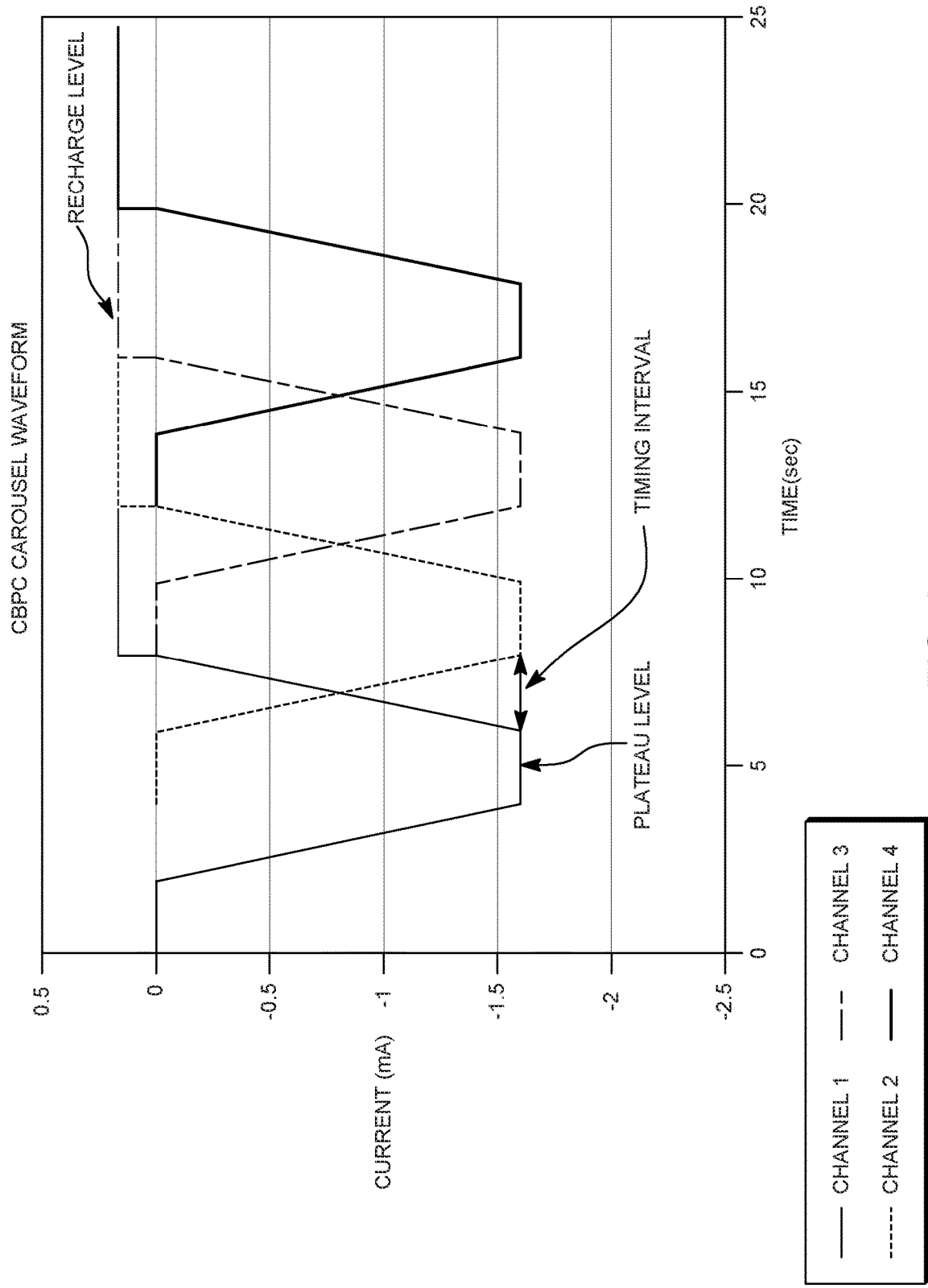
FIG. 6 is a plot illustrating the charge balanced polarizing current (CBPC) carousel waveform delivered by a four-contact nerve cuff.

A four contact nerve cuff electrode was fabricated with a carbon black coating. For each contact, the blocking waveform included a variable blocking phase followed by a square recharge phase. This pattern was repeated on each contact, as shown in FIG. 6.

Figure 7:
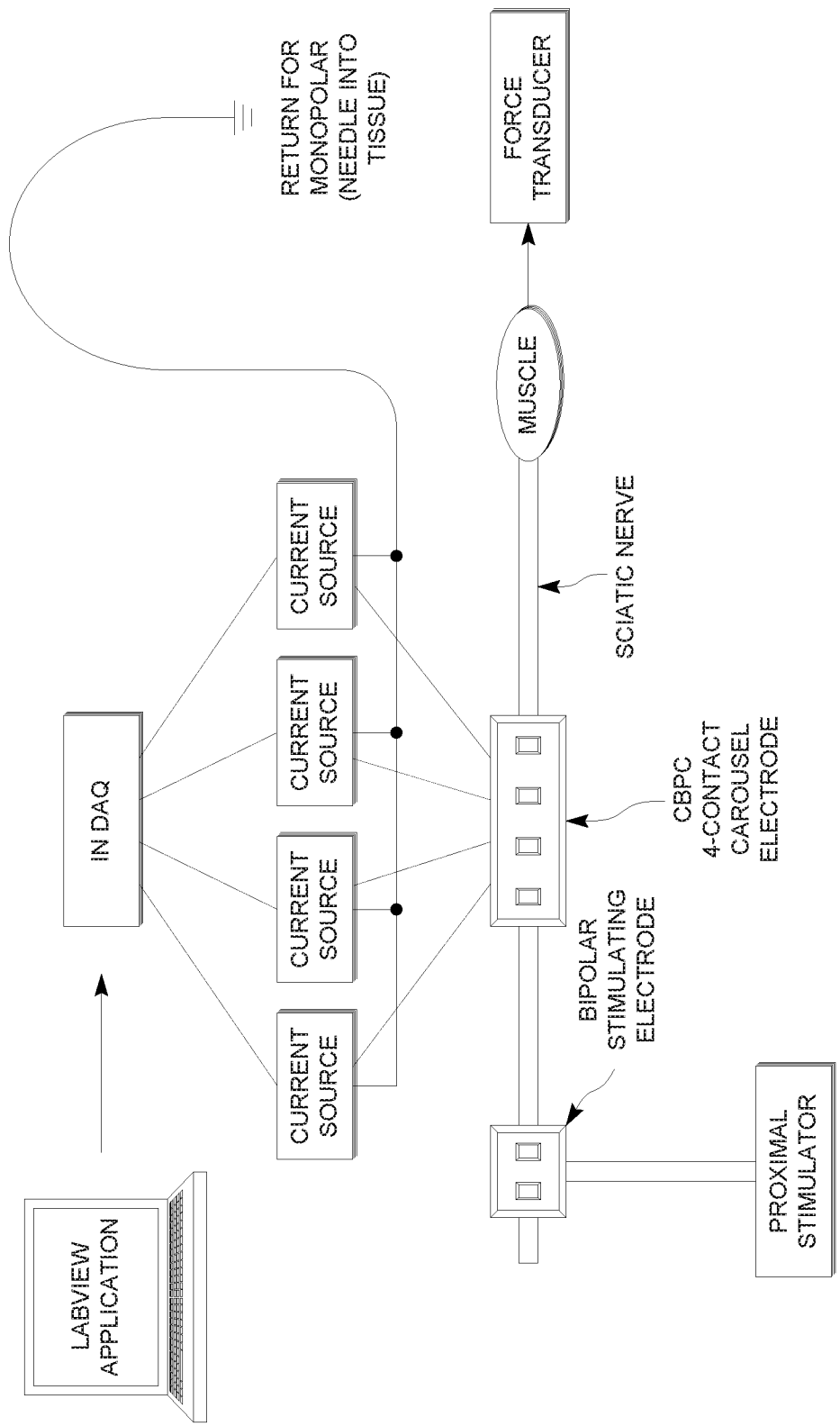
FIG. 7 is a diagram illustrating an experimental setup for delivering the CBPC carousel waveform to block conduction in a nerve.

As shown in FIG. 7, the sciatic nerve and the gastrocnemius muscle was dissected on a Sprague-Dawly rat. A proximal stimulating electrode was placed on the sciatic to initiate a measurable muscle twitch. The four contact blocking electrode was placed distally and attached to four current sources. Force output was evaluated by applying proximal stimulation at 1 Hz and then initiating a blocking waveform. The force output during block was measured and compared to the force output without block. The percent block was calculated by integrating the area of force during block and comparing to an extrapolated post block value based on the force measured before the block.

Figure 8:
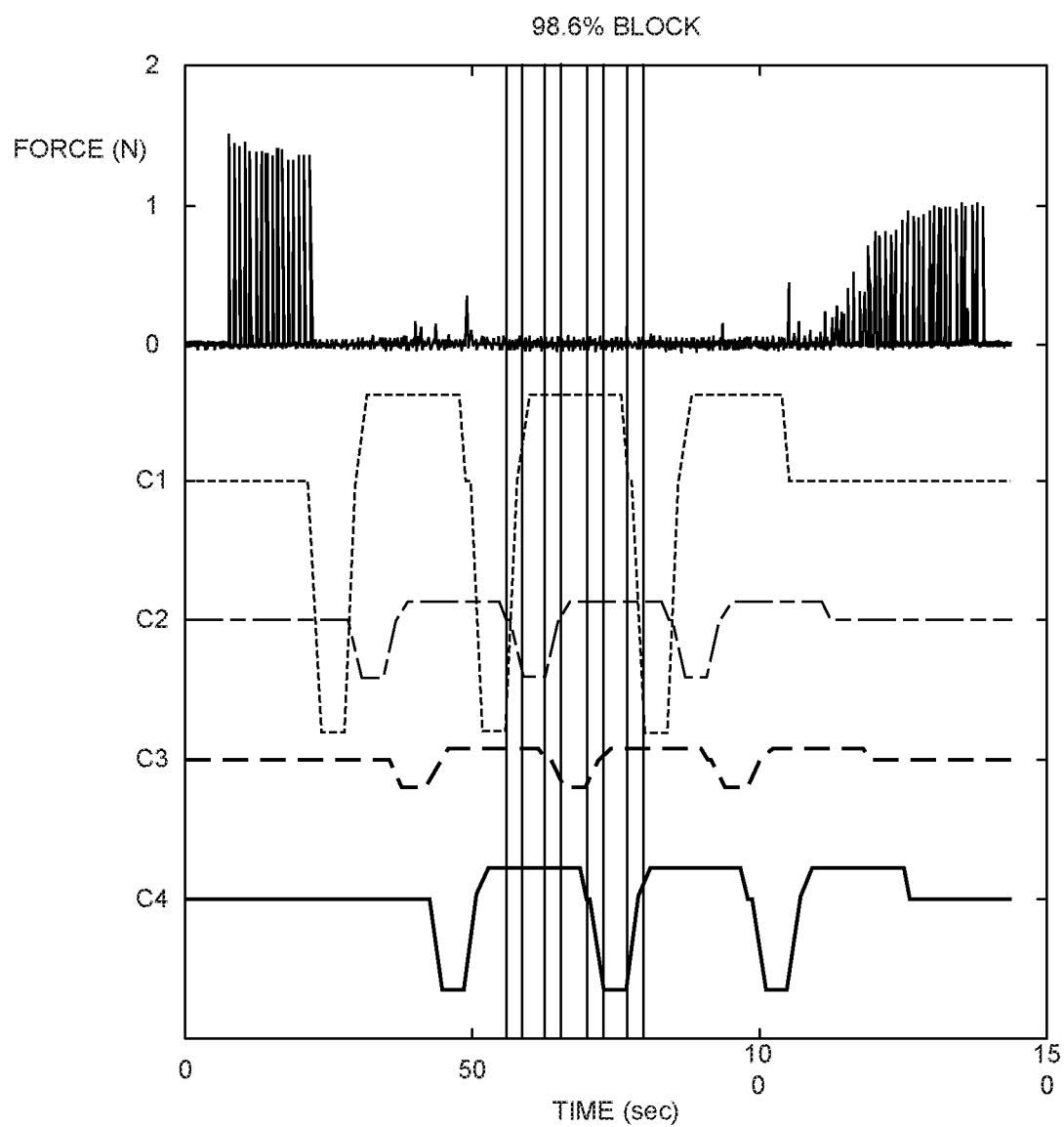
FIG. 8 is a plot illustrating a complete (98.6%) block with the CBPC carousel waveform.
Figure 9:
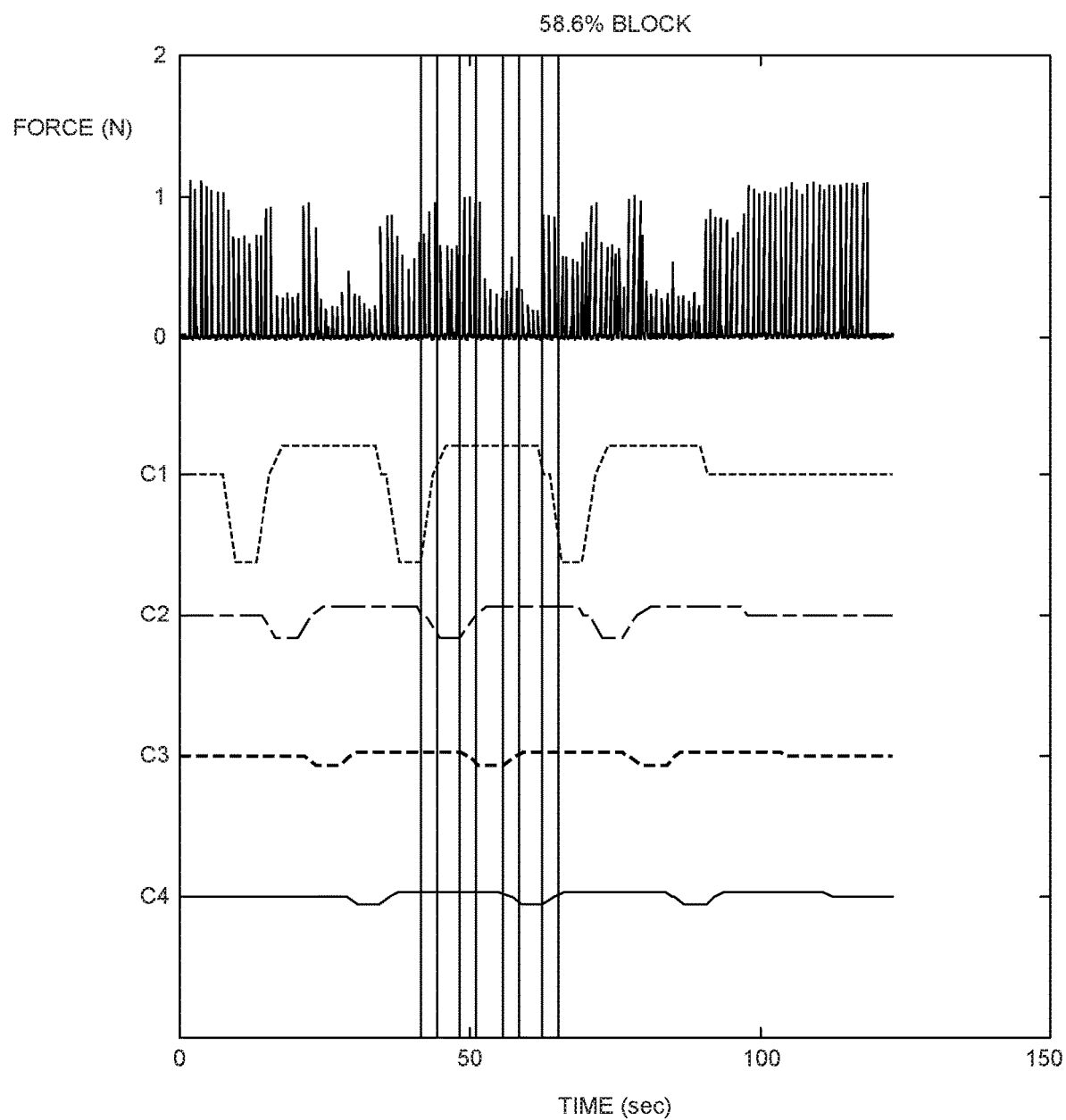
FIG. 9 is a plot illustrating a partial (58.6%) block with the CBPC carousel waveform.
Figure 10:
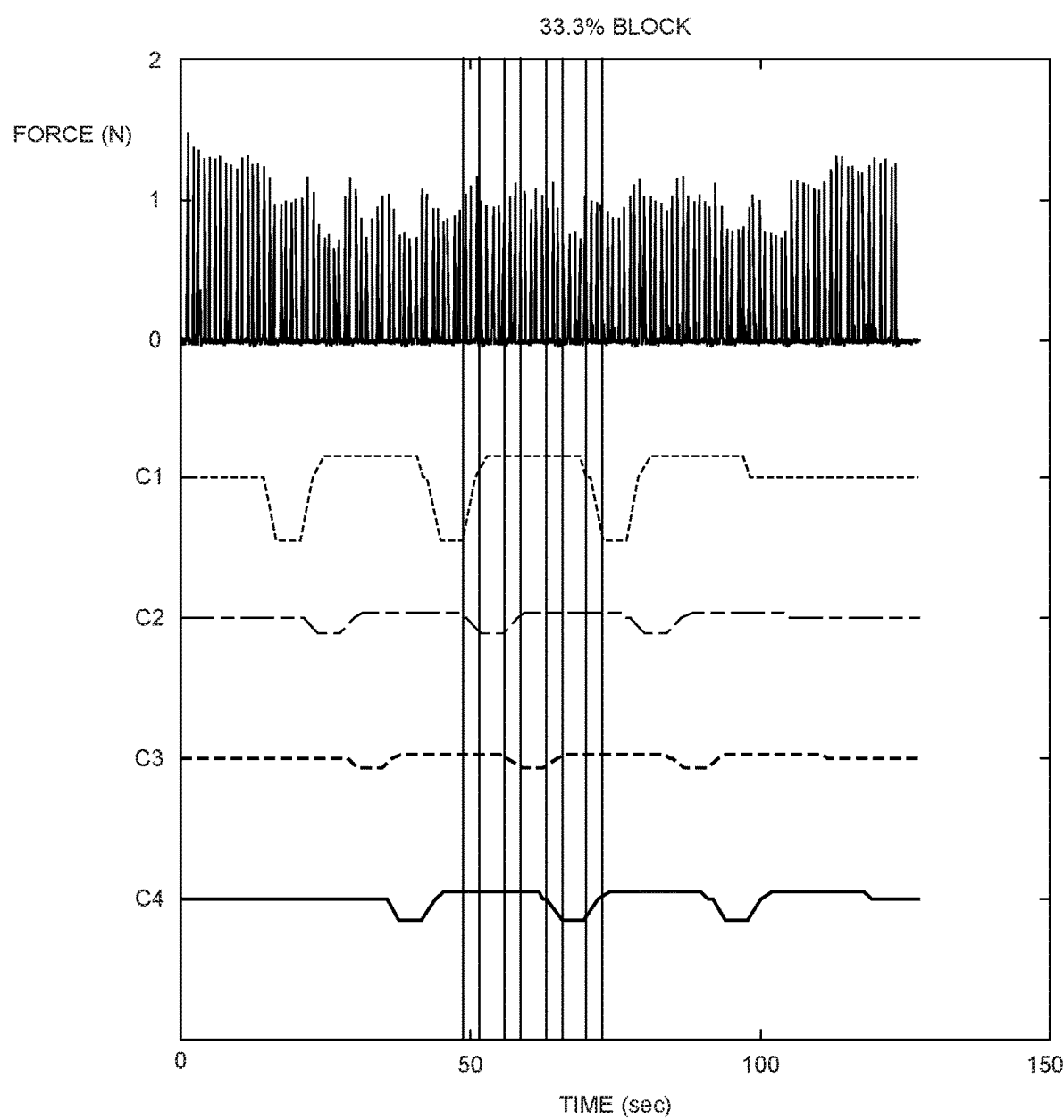
FIG. 10 is a plot illustrating a partial (33.3%) block with the CBPC carousel waveform.

As exemplified in FIG. 8, complete block (98.6%) can be achieved by maximizing the plateau for all the channels (−2.5, −0.8, −0.4, −1.3 mA). For partial block, pulses get through between the plateaus—as shown in FIG. 9 (58.6% block and FIG. 7 (33.3% block). This can be mitigated by spacing the pulses closer together. However, when the pulses are spaced more closely together, it is more difficult to complete the recharge phase of the first channel in time to overlap the pulses. This can be mitigated by increasing the recharge level. Increasing the recharge level causes interference between the channels, which increases the difficulty of achieving the partial block. However, supplementing the electrode with additional channels can make it easier to achieve smoother partial block.

The carousel design is highly dependent on the design of the electrode and the waveform parameters. Changes in electrode contact number, size and spacing can mitigate interference between the channels or allow for a smoother partial block. However, depending on the application, this may not be necessary.

Separated Nerve Interface Electrode (SINE)

Another solution that can provide block without spurious activity is the separated interface nerve electrode (SINE). The SINE electrode has the ability to provide a polarizing current block while separating any potentially damaging reactants from the nerve. However, partial block levels applied for long periods of time will progress to complete block, so a more advanced modulation scheme is needed.

Figure 11:
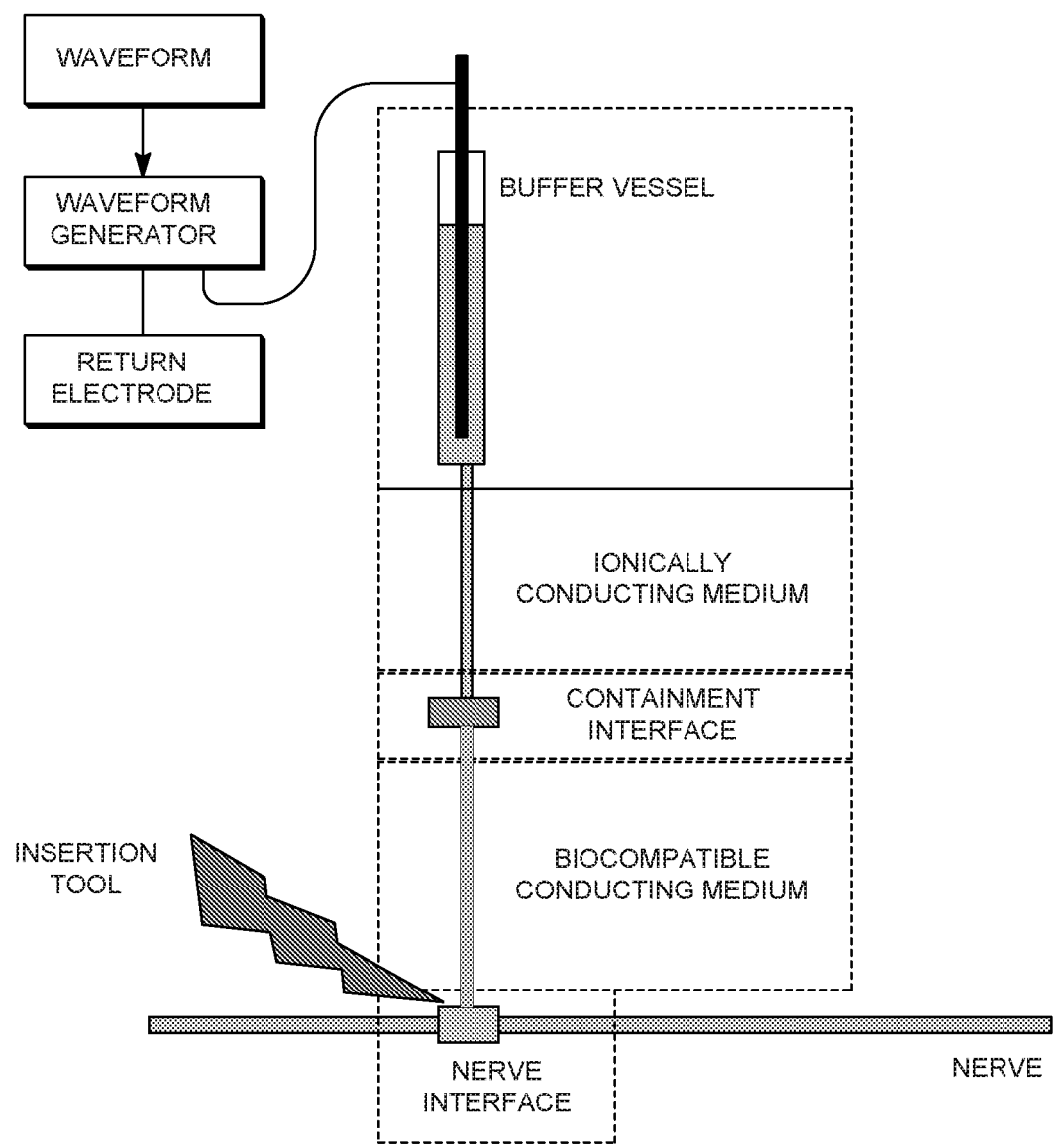
FIG. 11 diagram illustrating an experimental setup for using a separated interface nerve electrode (SINE) that can be used to deliver a nerve conduction block.

As shown in FIG. 11, the SINE electrode physically separates the metal electrode and the nerve cuff interface by a column of electrolyte. Any reactions that occur (e.g., electrochemical reactions at the electrode/electrolyte interface) are contained in the electrolyte. To improve the capacity of the SINE electrode, high surface area carbon (YP-50) was added to the saline to form a stiff paste. All of the carbon in the paste is electrochemically available for capacitive (double-layer) charging. The paste is concentrated enough so that it is both electrically conductive and ionically conductive. All carbon particles are electrically connected together. The solution is ionically continuous. A corrosion resistant graphite rod is used as a current collector. A syringe filter prevents the carbon from leaching out into the electrolyte connection down to the nerve. A current-controlled Keithley 6221 DC generator with a 105 Volt compliance was used to generate block. A silicone cuff was used to interface with the nerve. In vivo setup and data collection were the same as for the CBPC carousel.

Figure 12:
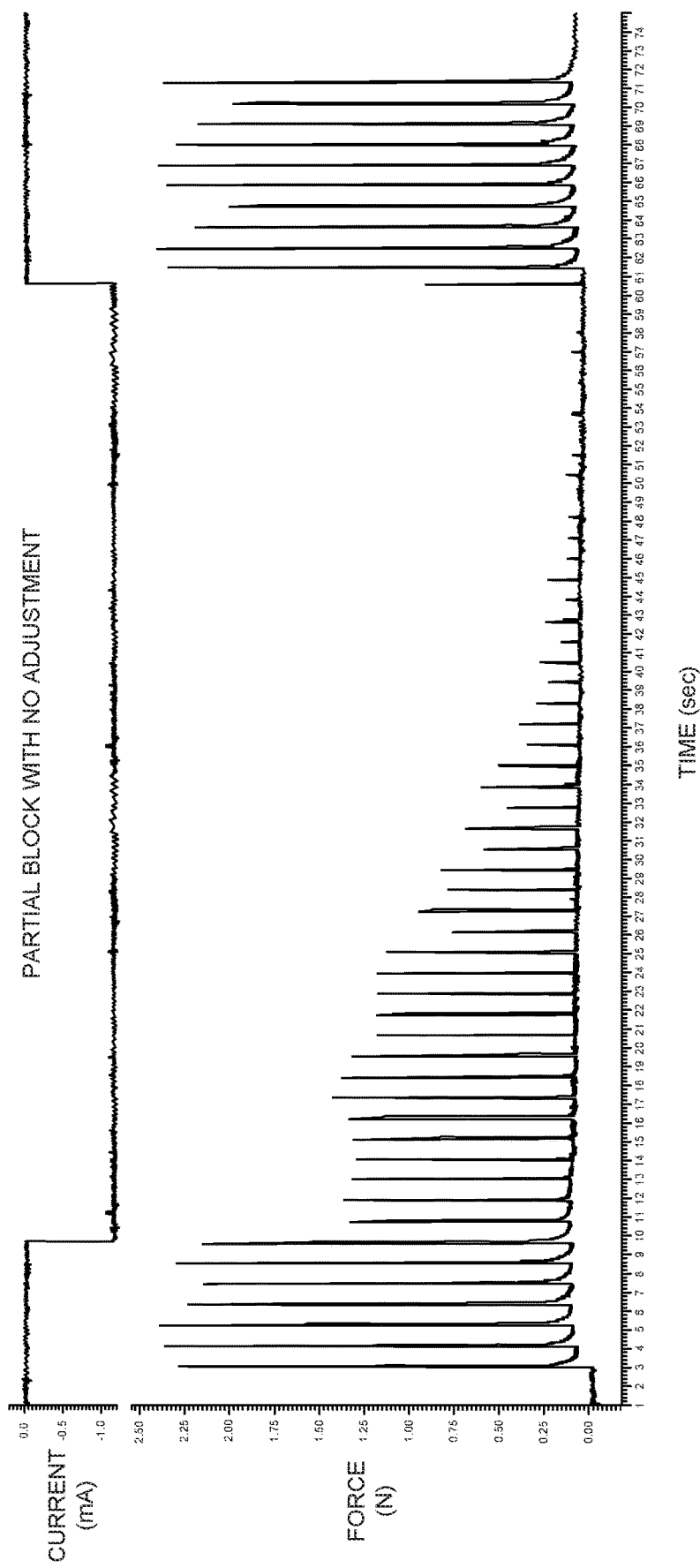
FIG. 12 is a plot showing partial block with no adjustment.
Figure 13:
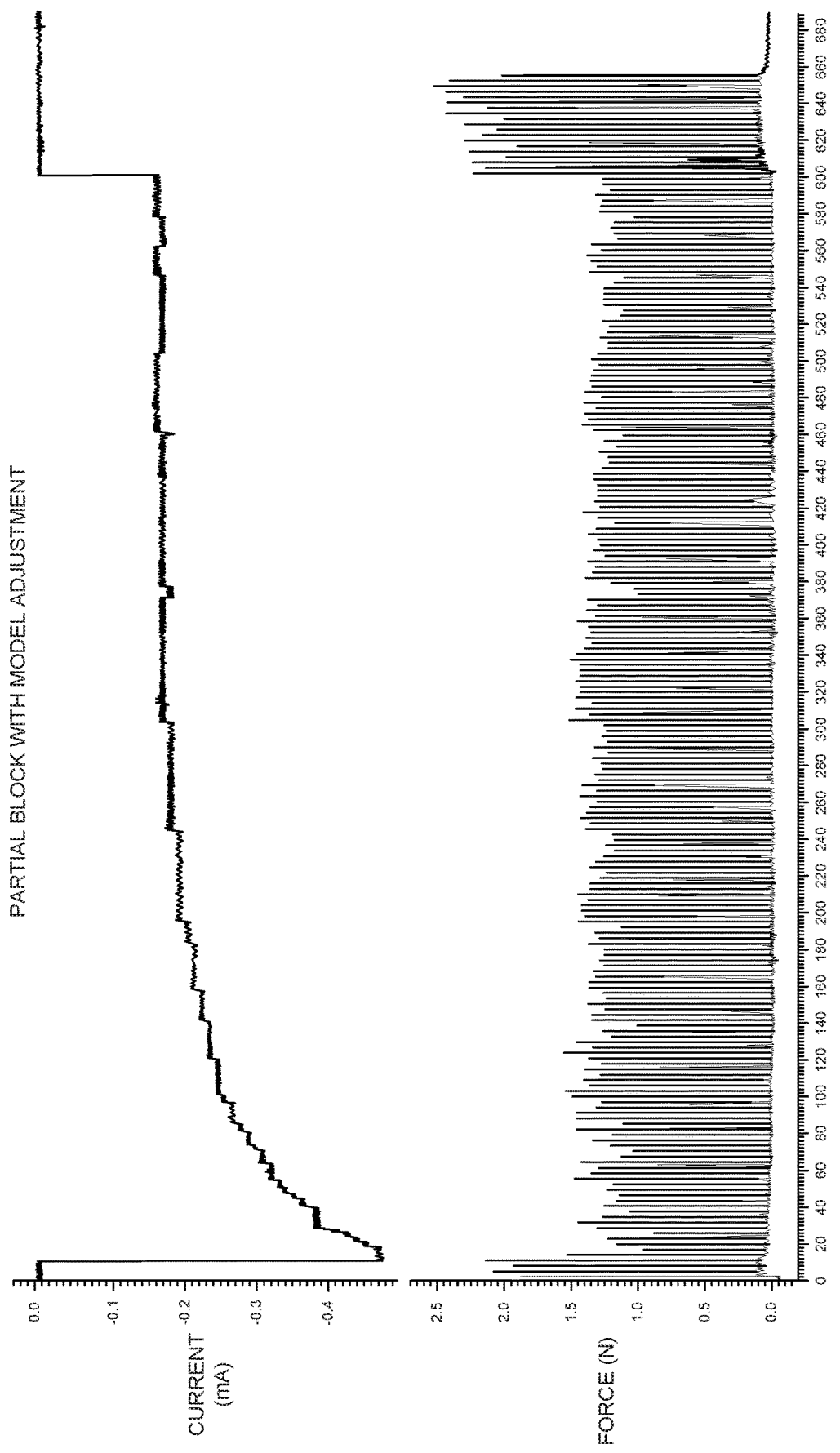
FIG. 13 is a plot showing partial block with a manual adjustment.
Figure 14:
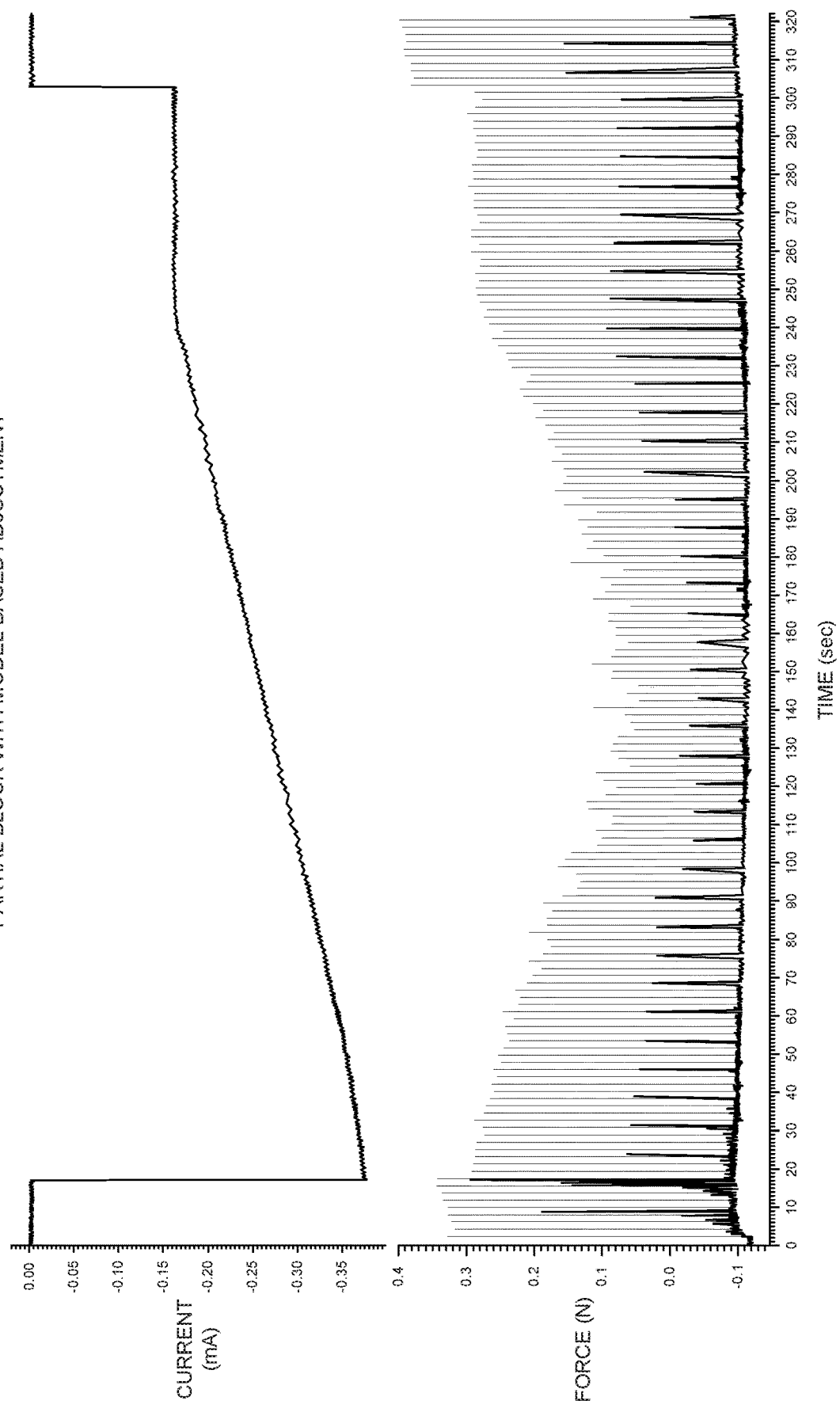
FIG. 14 is a plot illustrating a model based adjustment.

As shown in FIG. 12, the SINE may start as a partial block, but it progresses to greater levels of block. The partial block was maintained by manually adjusting the current level while monitoring a force output (FIG. 13). A simple proportional controller would be adequate to achieve this result autonomously. It may not always be possible to measure an output for a feedback controller, so a model-based controller would work if the system dynamics were estimated. An example of a control estimate using three inflection points is shown in FIG. 14. Controlling the SINE to deliver a constant partial block is primarily concerned with understanding the system dynamics and designing an appropriate controller.

VI. Examples

Direct current (DC) nerve conduction block is fast acting, reversible, onset free, and easy to modulate, making it ideal for a variety of applications in a patient's nervous system. The carousel design and the SINE show immense opportunities for expanding solutions to neurological diseases. Although some applications can be enhanced by complete nerve conduction block, many applications would be served by partial nerve conduction block, a less invasive solution.

It will be appreciated that the DC partial nerve conduction block can be applied to one or more neural structures related to the central nervous system, peripheral nervous system, autonomic nervous system, and enteric nervous system. However, described below are certain examples of some of the various medical conditions for which DC partial nerve conduction block can be used. The following examples are for the purpose of illustration only is not intended to limit the scope of the appended claims.

Motor System

In the motor system, spasticity is a debilitating condition that is a result of many different neurological conditions. A few examples of such neurological conditions include cerebral palsy, multiple sclerosis, spinal cord injury and stroke. In each example, the onset of spasticity results in many impairments and limitations including, but not limited to, gait disorders, fatigue, restricted range of movement, abnormal limb postures, quality of life issues, problems with activities of daily living, and/or pain, all of which impact the patient's quality of life. In addition to the quality of life impact of spasticity, the economic burden of any neurological condition increases significantly at the onset of spasticity. For stroke, it has been demonstrated that spasticity causes a four-fold increase in the direct costs associated with treating stroke patients. DC partial nerve conduction block can provide a solution that can minimize spasticity while maintaining muscle tone allowing for previously unattainable functional improvements.

Sensory System

In the sensory system, chronic neuropathic pain would be an ideal target for DC partial nerve conduction block. Neuropathic pain follows trauma or disease affecting the peripheral or central nervous system. Examples of such trauma can include physical trauma, spinal cord injury, while examples of such disease can be a side effect of chemotherapy, radiation, or surgery.

With some peripheral neuropathic pain, the source of the pain is localized at a neuroma. As is common with amputations, when a peripheral nerve is damaged, the peripheral nerve tries to regenerate itself towards the distal target. If the distal target is unavailable, axon sprouts grow into the surrounding scar tissue forming a neuroma, which can cause chronic pain and hypersensitivity. A neuroma is particularly well suited to DC partial nerve conduction block given the local nature of the condition. Also, the electrode used for DC partial nerve conduction block can easily be removed and placed in a different location, making the DC partial nerve conduction block desirable in the event that the neuroma changes in a way that lessens the effect of the nerve block.

Autonomic System

In the autonomic system, the properties of DC partial nerve conduction block provide a unique opportunity for modulation of neural activity. The autonomic nervous system frequently operates around a baseline of neural activity, which is modulated up or down to produce the desired physiological effects. For example, blood pressure is maintained through tonic activity in the autonomic nervous system. It would be extremely beneficial to not only be able to enhance neural activity, but also to inhibit neural activity in a graded/modulated manner Direct current can be modulated to affect a sub-population of axons to achieve a graded response. In the autonomic system, the onset response is particularly confounding since the effect is prolonged due to the dynamics of the system. The ability to produce an onset free nerve block is absolutely critical to provide an effect solution to autonomic diseases, and the subcutaneous nature of the block leads to greater use of the block throughout the medical community.

Regional Applications

Some regional applications are well suited to DC partial nerve conduction block intervention. As an example, damage to the occipital nerve can result in chronic headache symptoms. Pharmacological nerve blocks, which are often used to treat this condition, could easily be replaced with a minimally invasive DC partial nerve conduction block, which would provide a longer term relief. As another example, the pudendal nerve has successfully been blocked using KHFAC and nerve cuff electrodes for bladder control. Both of these methods could be enhanced by less invasive solution. Also, the DC would be capable of providing smooth transitions between partial and complete block which could further improve the functionality of the application.

From the above description, those skilled in the art will perceive improvements, changes and modifications. Such improvements, changes and modifications are within the skill of one in the art and are intended to be covered by the appended claims.

The invention claimed is:

1. A method comprising:
   configuring, by a waveform generator, one or more direct current waveforms to provide a level of current to provide a stable, continuous, partial block to a neural structure for a time period;
   delivering the one or more direct current waveforms through one or more electrodes to provide the stable, continuous, partial block continuously at a block level to the neural structure for the time period, wherein the one or more electrodes comprise a separated interface nerve electrode (SINE);
   providing feedback to the waveform generator to maintain the stable, continuous, partial block at the block level, wherein the feedback comprises:
   monitoring a property associated with a stability of the stable, partial block to determine if the property is outside a preset range for a desired partial block to the neural structure in response to application of the one or more direct current waveforms over the time period; and
   when the property is determined to be outside the preset range, altering a parameter associated with the one or more direct current waveforms to maintain the property within the preset range after application of the one or more direct current waveforms over the time period.

2. The method of claim 1, wherein the neural structure comprises at least one of tissue related to the central nervous system, peripheral nervous system, autonomic nervous system, and enteric nervous system.

3. The method of claim 1, wherein the property associated with the stability of the stable, partial block comprises a physiological output controlled by the neural structure produced in response to application of the stable, continuous, partial block and the parameter associated with the one or more direct current waveforms comprises another level of the current of the one or more direct current waveforms to maintain the stable, continuous partial block at the block level.

4. The method of claim 1, wherein the feedback is performed automatically by a controller.

5. The method of claim 4, wherein the controller is a simple proportional controller.

6. The method of claim 1, wherein the one or more electrodes comprise at least two electrode contacts in a nerve cuff and the one or more DC waveforms comprise a variable blocking phase followed by a recharge phase repeated for each contact.

7. The method of claim 6, wherein the property associated with the stability of the stable, continuous, partial block comprises a physiological output controlled by the neural structure produced in response to application of the stable, partial block and the parameter associated with the one or more direct current waveforms comprises a recharge level or a spacing between pulses in the blocking phases.

8. The method of claim 7, wherein the physiological output is a force provided by a muscle.

9. The method of claim 1, wherein the parameter associated with the one or more direct current waveforms is a current level, a recharge level, or a spacing between pulses of the one or more direct current waveforms.

10. A system comprising:
- a waveform generator to generate one or more direct current (DC) waveforms configured to provide a level of current to provide a stable, continuous, partial block to a neural structure for a time period;
- one or more electrodes to deliver the one or more direct current waveforms to provide the stable, continuous, partial block continuously at a block level to the neural structure for the time period, wherein the one or more electrodes comprise a separated interface nerve electrode (SINE);
- a feedback device to provide feedback to the waveform generator to maintain the stable, continuous, partial block, wherein the feedback is based on:
  - a monitored property associated with the stability of the stable, continuous, partial block at the block level, wherein the property is monitored to in response to application of the one or more direct current waveforms over the time period to determine whether the property is outside a preset range for a desired partial block to the neural structure; and
  - an altered parameter associated with the one or more direct current waveforms that is altered to maintain the property within the preset range in response to determining the property is outside the preset range after application of the one or more direct current waveforms over the time period.

11. The system of claim 10, wherein the feedback device comprises a controller comprising a non-transitory memory and a processor.

12. The system of claim 11, wherein the controller is a proportional controller.

13. The system of claim 10, wherein the monitored property comprises a physiological output controlled by the neural structure produced in response to application of the stable, continuous, partial block and the parameter associated with the one or more direct current waveforms comprises another level of current associated with the one or more direct current waveforms to maintain the stable, continuous partial block at the block level.

14. The system of claim 10, wherein the direct current waveform comprises a constant level direct current waveform, a varying level direct current waveform, a direct current waveform followed by a recharge phase, or a direct current waveform in combination with a high frequency signal.

* * * * *